United States Patent
Horn et al.

(10) Patent No.: US 7,951,581 B2
(45) Date of Patent: *May 31, 2011

(54) METHOD AND REAGENT SYSTEM WITH NON-REGENERABLE ENZYME-COENZYME COMPLEX

(75) Inventors: Carina Horn, Biblis (DE); Joachim Hoenes, Zwingenberg (DE); Wolfgang-Reinhold Knappe, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 412 days.

This patent is subject to a terminal disclaimer.

(21) Appl. No.: 12/008,283

(22) Filed: Jan. 10, 2008

(65) Prior Publication Data

US 2008/0182324 A1    Jul. 31, 2008

Related U.S. Application Data

(62) Division of application No. 10/514,451, filed as application No. PCT/EP03/05178 on May 16, 2003, now Pat. No. 7,341,830.

(30) Foreign Application Priority Data

| May 16, 2002 | (DE) | ................................ | 102 21 840 |
| May 16, 2002 | (DE) | ................................ | 102 21 845 |
| May 16, 2002 | (DE) | ................................ | 102 21 846 |

(51) Int. Cl.
*C12M 1/00*   (2006.01)
*C12Q 1/00*   (2006.01)

(52) U.S. Cl. ........................................ 435/287.1; 435/4

(58) Field of Classification Search .................. None
See application file for complete search history.

(56) References Cited

U.S. PATENT DOCUMENTS

| 3,964,974 A | 6/1976 | Banauch et al. |
| 4,451,568 A | 5/1984 | Schneider et al. |
| 4,820,399 A | 4/1989 | Senda et al. |
| 4,919,767 A | 4/1990 | Vadgama et al. |
| 5,059,526 A * | 10/1991 | Arai et al. ........................ 435/17 |
| 5,340,722 A | 8/1994 | Wolfbeis et al. |
| 5,447,847 A | 9/1995 | Yamada et al. |
| 7,553,615 B2 | 6/2009 | Heindl et al. |
| 2008/0213808 A1 | 9/2008 | Knappe |
| 2008/0219809 A1 | 9/2008 | van der Meulen et al. |
| 2009/0246818 A1 | 10/2009 | Heindl et al. |
| 2010/0227348 A1 | 9/2010 | Petrich et al. |

FOREIGN PATENT DOCUMENTS

| DE | 4118880 C2 | 12/1992 |
| EP | 0327952 A1 | 4/1992 |
| EP | 0691408 B1 | 1/1996 |
| JP | 7115997 | 5/1995 |
| JP | 7115998 | 5/1995 |
| JP | 9248200 | 9/1997 |
| JP | 2000035413 | 2/2000 |
| JP | 2001149092 | 6/2001 |

OTHER PUBLICATIONS

D'Auria Sabato et al.: "The fluorescence emission of the apoglucose oxidase from aspergillus niger as probe to estimate glucose concentrations". Biochemical and Biophysical Research Communications, Acedemic Press Inc., Orlando, FL, US., vol. 263, No. 2, 1999, pp. 550-553, XP002158779; ISSN: 0006-291X.

Sierra et al.: "Determination of Glucose in Blood on the Instrinsic Fluorescence of Glucose Oxidase", Analytical Chemistry, vol. 69, No. 8, Apr. 15, 1997, pp. 1471-1476.

Narayanaswamy et al.: An optical Fibre Probe for the Determination of Glucose Based on Immobilized Glucose Dehydrogenase, Analytical Letters 21 (7), 1998, pp. 1165-1175.

Gemba, "Series 1 enzyme test basic knowledge of daily test", KK Igaku-Shoin, pp. 88, 92-95, 2nd published, 1976.

Gemba, "Series 1 enzyme test basic knowledge of daily test", KK Igaku-Shoin, pp. 16-18, 2nd published, 1976.

* cited by examiner

*Primary Examiner* — Rebecca E. Prouty
*Assistant Examiner* — Paul C. Martin
(74) *Attorney, Agent, or Firm* — Justin L. Sage; Roche Diagnostics Operations, Inc.

(57) ABSTRACT

The present invention is generally directed towards a reagent system for detecting an analyte in a sample. The reagent system has a detection reagent comprising an enzyme-coenzyme complex in a form such that no regeneration of the coenzyme takes place, whereby the enzyme-coenzyme complex is employed in an at least stoichiometric amount relative to the analyte present in the sample, and a support to receive the detection reagent.

12 Claims, 5 Drawing Sheets

METHOD AND REAGENT SYSTEM WITH NON-REGENERABLE ENZYME-COENZYME COMPLEX

The present application is a divisional application based on and claiming priority to U.S. application Ser. No. 10/514,451, filed May 26, 2005, which was as of the actual filing date of the present application, and which is now U.S. Pat. No. 7,341,830 issued Mar. 11, 2008, which is a §371 of PCT/EP03/05178 filed May 16, 2003 which claims the benefit of priority to German Application Nos. 10221512.5 filed May 16, 2002, 10221840.4 filed May 16, 2002, and 10221846.3 filed May 16, 2002.

TECHNICAL FIELD

The invention relates to a method and a reagent system for detecting an analyte in a sample through an enzymatic reaction, comprising the use of an enzyme-coenzyme complex as non-regenerable, in particular stoichiometric reactant for the analyte present in the sample.

The detection of analytes, for example glucose in blood, by enzymatic methods is known. These entail the analyte to be determined being brought into contact with a suitable enzyme and a coenzyme, the enzyme being employed in catalytic amounts. The redox equivalents produced on reduction or oxidation of the coenzyme are transferred to mediators which are then detected electrochemically or photometrically in a further step. A calibration provides a direct connection between the measurement and the concentration of the analyte to be determined.

BACKGROUND

Sierra et al. (Anal. Chem. 69 (1997), 1471-1476) describe a determination of blood glucose based on the intrinsic fluorescence of glucose oxidase. In this method too, the enzyme is employed together with its coenzyme FAD in catalytic amounts, with redox equivalents being transferred to oxygen as mediator.

Narayanaswamy et al. (Analytical Letters 21 (7) (1988), 1165-1175) describe a fluorescence measurement with glucose dehydrogenase and NAD for glucose determination. The enzyme is in this case employed in catalytic, i.e. non-stoichiometric, amounts. The fluorescence measurement detects the free NADH in the solution.

It is possible through the electrochemically active substances (mediators) required for the prior art detection systems to detect the analytes to be determined only indirectly, i.e. via a plurality of chemical reactions. For this purpose, a complicated adjustment of the concentrations of the substances involved to optimize the reaction rate is often necessary. There is moreover the risk that the required electrochemically active substances are unstable on prolonged storage.

The mediators often also have to be employed in large excess relative to the enzyme-coenzyme system. The coenzyme has a high reactivity, so that the enzymic activity declines markedly on decomposition of the mediator, even in small amounts, e.g. <1% or on exposure to foreign substances, e.g. volatilization of the substances from packaging materials. This may lead to false signals in the determination of the analyte. Yet a further disadvantage is that the determination times for the analytes are normally in the region of at least a few seconds, for example for glucose in the region of >4 s, and the required sample volumes are large, e.g. >0.5 µl.

The object on which the present invention was based is at least partly to avoid the described disadvantages of the prior art. It was particularly intended to provide a non-sensitive and rapid method for the enzymatic detection of analytes, which leads to reliable measurement results even in the absence of mediators or/and indicators.

This object is achieved by using an enzyme-coenzyme complex as stoichiometric reactant instead of, as usual, as catalyst. Detection of the analyte requires only a single reaction step and is therefore extremely fast. The use of mediators and indicators, associated with the employment of complex reaction mixtures, with low stability and high susceptibility to interference, is no longer necessary.

SUMMARY

It is against the above background that the present invention proves certain unobvious advantages and advancements over the prior art. In particular, the inventor has recognized a need for improvements in a method and reagent system with non-regenerable enzyme-coenzyme complex.

Although the present invention is not limited to specific advantage or functionality, it is noted that the present invention provides one aspect of the invention is thus a method for detecting an analyte in a sample by an enzymatic reaction, comprising the steps:

contacting the sample with a detection reagent comprising an enzyme-coenzyme complex, where no regeneration of the coenzyme takes place, and detecting a reaction of the analyte through a change in the enzyme-coenzyme complex.

A further aspect of the invention is a reagent system for detecting an analyte in a sample, comprising:

a detection reagent comprising an enzyme-coenzyme complex, where no regeneration of the coenzyme takes place, and a support to receive the detection reagent.

The present invention makes a simple qualitative or quantitative determination of analytes possible within a very short reaction time of, preferably, $\leq 5$ s, particularly preferably $\leq 1$ s, most preferably $\leq 0.1$ s. The reaction is carried out under conditions with which no regeneration of the coenzyme takes place during the determination. It is moreover possible for a molecule enzyme-coenzyme complex to react only with a single molecule of the analyte. The reaction is therefore expediently carried out in the absence of mediators or other substances able to bring about regeneration of the coenzyme.

The detection reagent comprises the enzyme-coenzyme complex in an amount sufficient to make qualitative or/and quantitative determination of the analyte possible according to the desired test format. In particular, for quantitative determination of the analyte, the enzyme-coenzyme complex is employed in an amount such that the number of reacting molecules of the enzyme-coenzyme complex correlates with the analyte concentration present in the sample. The enzyme-coenzyme complex is particularly preferably employed in an at least stoichiometric amount relative to the analyte present in the sample, preferably in a stoichiometric excess relative to the analyte. In this connection, the statement "in at least a stoichiometric amount" means that the size of the sample is adjusted relative to the number of molecules of the enzyme-coenzyme complex in such a way that, with the analyte concentrations to be expected in the sample, the number of molecules of the enzyme-coenzyme complex which react with the analyte correlates with the analyte concentration present in the sample. "Stoichiometric amount" preferably means that the number of molecules of the enzyme-coenzyme complex corresponds to the maximum number of analyte molecules to be expected in the investigative sample.

The method and the detection system permit the use of very small amounts of sample, for example sample volumes of $\leq 1$ μl, in particular $\leq 0.1$ μl. The sample can where appropriate also be diluted before contacting with the detection reagent.

The method and detection system of the invention is suitable for determining any analytes, for example parameters in body fluids such as, for example, blood, serum, plasma or urine, but also in effluent samples or foodstuffs. The method can also be carried out as wet test, e.g. in a cuvette, or as dry test on an appropriate reagent support.

The analytes which can be determined are any biological or chemical substances which are able to undergo a reaction, in particular a redox reaction, with an enzyme-coenzyme complex, such as, for example, glucose, lactic acid, malic acid, glycerol, alcohol, cholesterol, triglycerides, ascorbic acid, cysteine, glutathione, peptides etc.

The enzymatic reaction is preferably a redox reaction in which the coenzyme in the enzyme-coenzyme complex is reduced or oxidized. The enzyme preferably used for a reaction of this type is an oxidoreductase. The enzyme particularly preferably used is a dehydrogenase, for example selected from a glucose dehydrogenase (E.C.1.1.1.47), lactate dehydrogenase (E.C.1.1.1.27, 1.1.1.28), malate dehydrogenase (E.C.1.1.1.37), glycerol dehydrogenase (E.C.1.1.1.6), alcohol dehydrogenase (E.C.1.1.1.1) or amino-acid dehydrogenase, e.g. L-amino-acid dehydrogenase (E.C.1.4.1.5). Further suitable enzymes are oxidases such as, for example, glucose oxidase (E.C.1.1.3.4) or cholesterol oxidase (E.C.1.1.3.6).

Coenzymes for the purposes of the present invention are preferably organic molecules which are linked covalently or noncovalently to an enzyme and are changed, for example oxidized or reduced, by the conversion of the analyte. Preferred examples of coenzymes are flavin, nicotine and quinone derivatives, for example flavin nucleoside derivatives such as, for example, FAD, $FADH_2$, FMN, $FMNH_2$, etc., nicotine nucleoside derivatives such as, for example, $NAD^+$, $NADH/H^+$, $NADP^+$, $NADPH/H^+$ etc. or ubiquinones such as, for example, coenzyme Q, PQQ etc.

The change in the coenzyme through reaction with the analyte can in principle be detected in any manner. It is possible in principle to employ for this all methods known in the art for detecting enzymatic reactions. However, the change in the coenzyme is preferably detected by optical methods. Optical detection methods include for example measuring absorption, fluorescence, circular dichroism (CD), optical rotary dispersion (ORD), refractometry etc. The change in the coenzyme is particularly preferably detected by measuring the fluorescence. The fluorescence measurement is highly sensitive and makes it possible to detect even low concentrations of the analyte in miniaturized systems.

The method or detection system of the invention may comprise a liquid test, in which case the reagent is present for example in the form of a solution or suspension in an aqueous or nonaqueous liquid or as powder or lyophilizate. However, the method and detection system of the invention preferably comprises a dry test, in which case the reagent is applied to a support. The support may comprise for example a test strip comprising an absorbent or/and swellable material which is wetted by the sample liquid to be investigated.

In a particularly preferred embodiment, the detection reagent used is a gel matrix with an enzyme-coenzyme complex embedded therein. The gel matrix preferably has a layer thickness of $\leq 50$ μm, in particular $\leq 5$ μm, and is applied to a support, for example an at least partly optically transparent support. The gel matrix may be a matrix comprising one or more soluble polymers, as in known dry test systems (e.g. AccuChek Active), and can be produced by knife application and drying. The matrix is preferably a polymer with a structure based on photopolymerizable substances such as, for example, acrylic monomers, e.g. acrylamide or/and acrylic esters such as polyethylene glycol diacrylate, or vinylaromatic monomers, e.g. 4-vinylbenzenesulfonic acid, or combinations thereof. A gel matrix of this type can be produced by applying a liquid which contains the reagent, comprising enzyme, photopolymerizable monomer and, where appropriate, coenzyme, photoinitiator or/and unreactive constituents, to an at least partly optically transparent support, for example to a plastics sheet, and irradiating, for example with UV light from the reverse side, so that polymerization of the monomer or of the monomers takes place on the support up to a predefined layer thickness. The layer thickness can be controlled by adding absorbing substances to the reagent or/and through the duration or intensity of irradiation. Excess liquid reagent can be removed and reused after the polymerization (see, for example, FIG. 2).

On the other hand, the gel matrix can also be produced by conventional coating procedures, in which case the liquid reagent is applied to a support, brought to the desired thickness using suitable methods, e.g. using a knife, and then completely polymerized.

After inclusion by polymerization or embedding in the gel matrix, the enzyme is in a protected microenvironment. If the polymeric gel matrix is sufficiently crosslinked, the enzyme molecules are present in an immobilized form. Low molecular weight substances or glucose or other analytes or else coenzymes can, however, diffuse freely through the polymer network.

The enzyme can either be included together with its coenzyme by polymerization in the matrix or, after the polymerization, the matrix can be brought into contact with a solution of the coenzyme, so that the appropriate enzyme-coenzyme complex is formed. The concentration of the enzyme in the gel matrix is preferably chosen to be high enough for a stoichiometric reaction with the analyte to be determined, and a direct determination of the coenzyme which is changed by the reaction, to be possible. The reaction consists only of a single catalytic reaction, for example, a redox reaction, which can take place in the region of milliseconds or microseconds. The coenzyme which is changed by the reaction is optimally protected from interfering influences through binding to the active center of the enzyme and, where appropriate, additionally by embedding in the gel matrix.

The invention is additionally to be explained by the following figures and examples.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
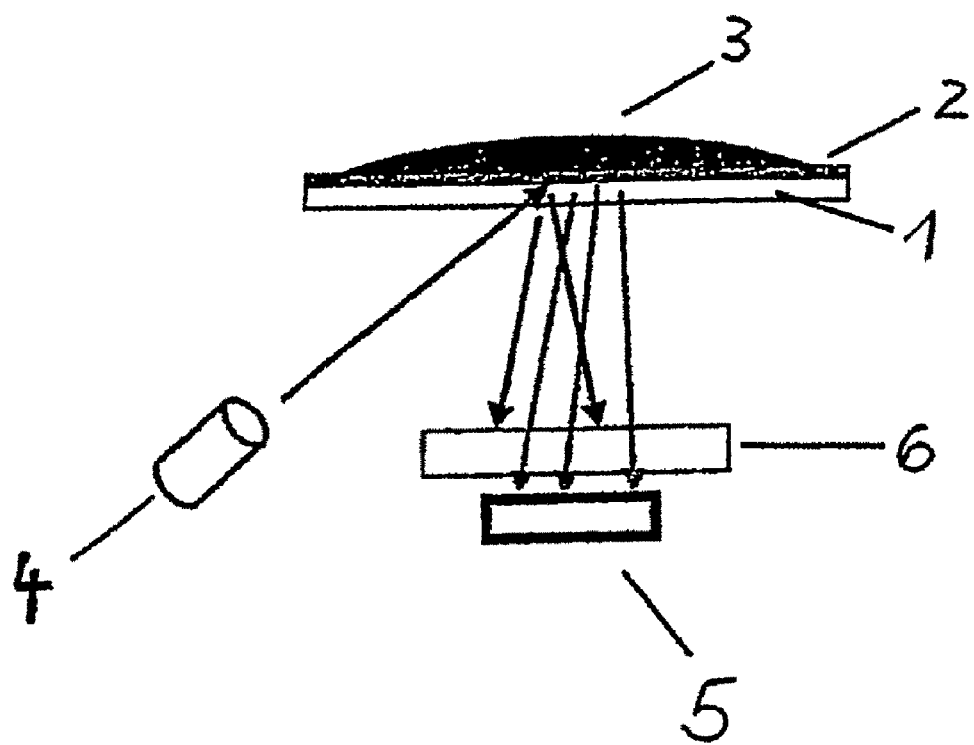
FIG. 1 shows a first embodiment of the detection system of the invention. A reagent layer (2), e.g. a gel matrix with an enzyme-coenzyme complex, is applied to an optically transparent support (1). The enzyme-coenzyme complex is in a form such that no regeneration of the coenzyme can take place during the analyte determination. A sample (3), e.g. blood, is put on the reagent layer. Determination of the enzymatic reaction between the analyte contained in the sample (3), and the enzyme-coenzyme complex contained in the reagent layer (2) takes place by optical methods. Light from a light source (4), e.g. a laser or an LED, is beamed from behind (through the support) onto the reagent layer (2). Absorption light or fluorescent light beamed back from the sample is detected in a detector (5). Where appropriate—in particular for detecting fluorescent light—an optical filter element (6) is put in front of the detector in order to block leakage of the fluorescence-exciting light.
Figure 2:
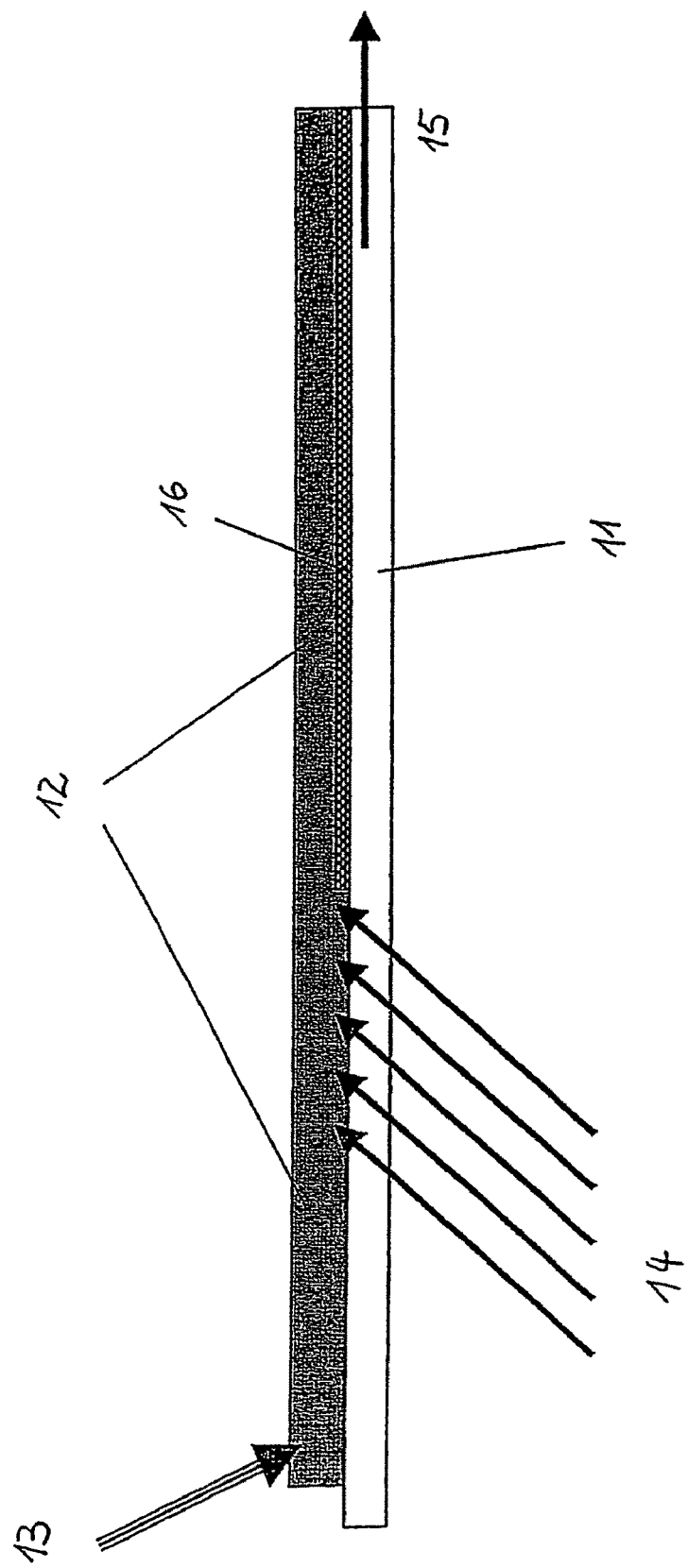
FIG. 2 shows the production of a detection system of the invention. A liquid reagent (12) is applied, for example in a first position (13), to an optically transparent support (11), e.g. a plastics sheet. The liquid reagent (12) is irradiated at a second position from below through the support (11) with light from a light source (14). At the same time, the support is moved in the direction (15) identified by the arrow. A polymerized reagent layer (16) is formed directly on the support (11). Excess liquid reagent is present above the polymer layer (16). The thickness of the polymerized reagent layer (16) can be controlled through the reagent composition, the duration and intensity of the beaming in of light, and through the properties of the support (11).
Figure 3:
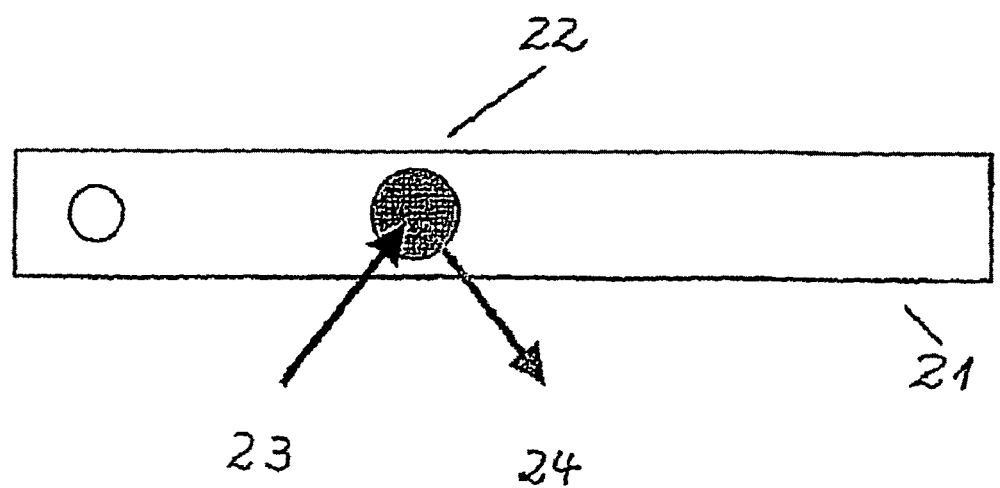
FIG. 3 shows an embodiment of a fluorescence-based sensor from below. A polymerized reagent layer, for example one produced by the continuous process in FIG. 2, can be cut and applied to a support (21) by use of known techniques. After application of the sample to the upper side, exciting light (23), e.g. UV light, is beamed in from a light source from below. The fluorescence (24), e.g. blue light, generated through the reaction of the analyte with the enzyme-coenzyme complex in the reagent layer (22) is detected with a detector.
Figure 4:
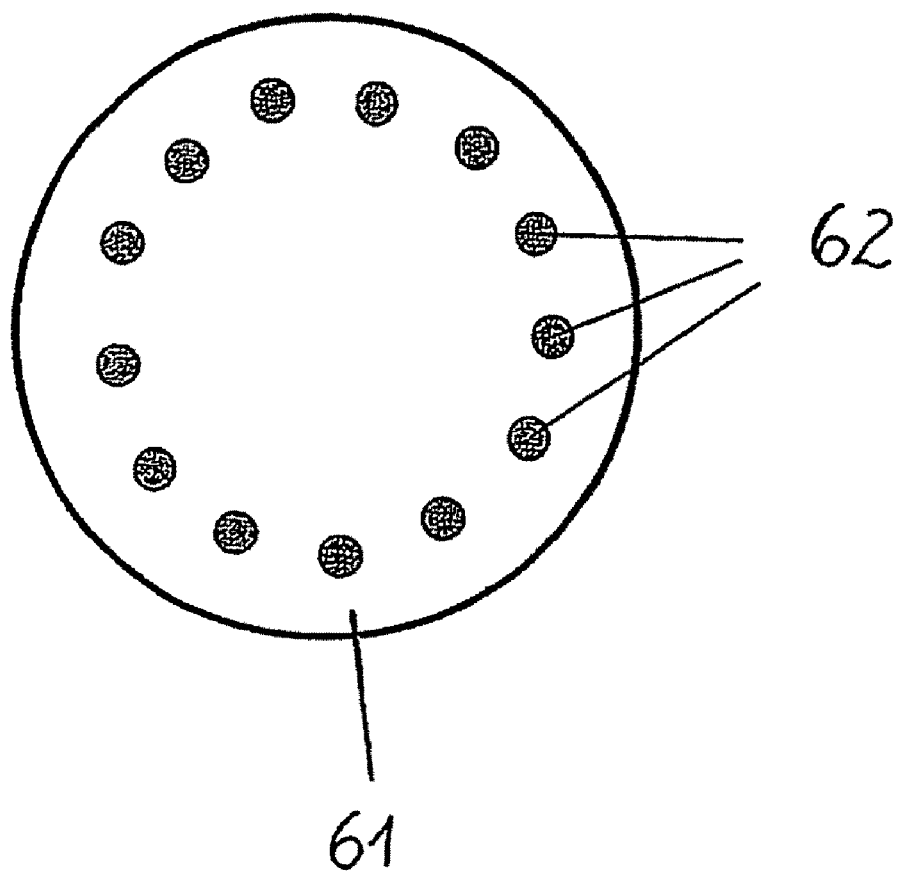

It is also possible for a plurality of (identical or different) reagents to be applied to a support. One example of such an embodiment in the form of a disk is shown in FIG. 4. A plurality of reagent spots (62) is disposed on the optically transparent support (61).

Figure 5:
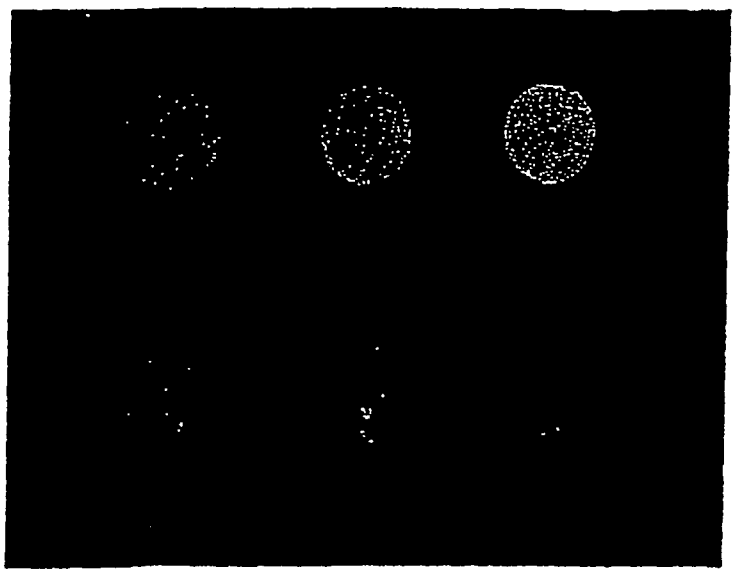
Figure 5:
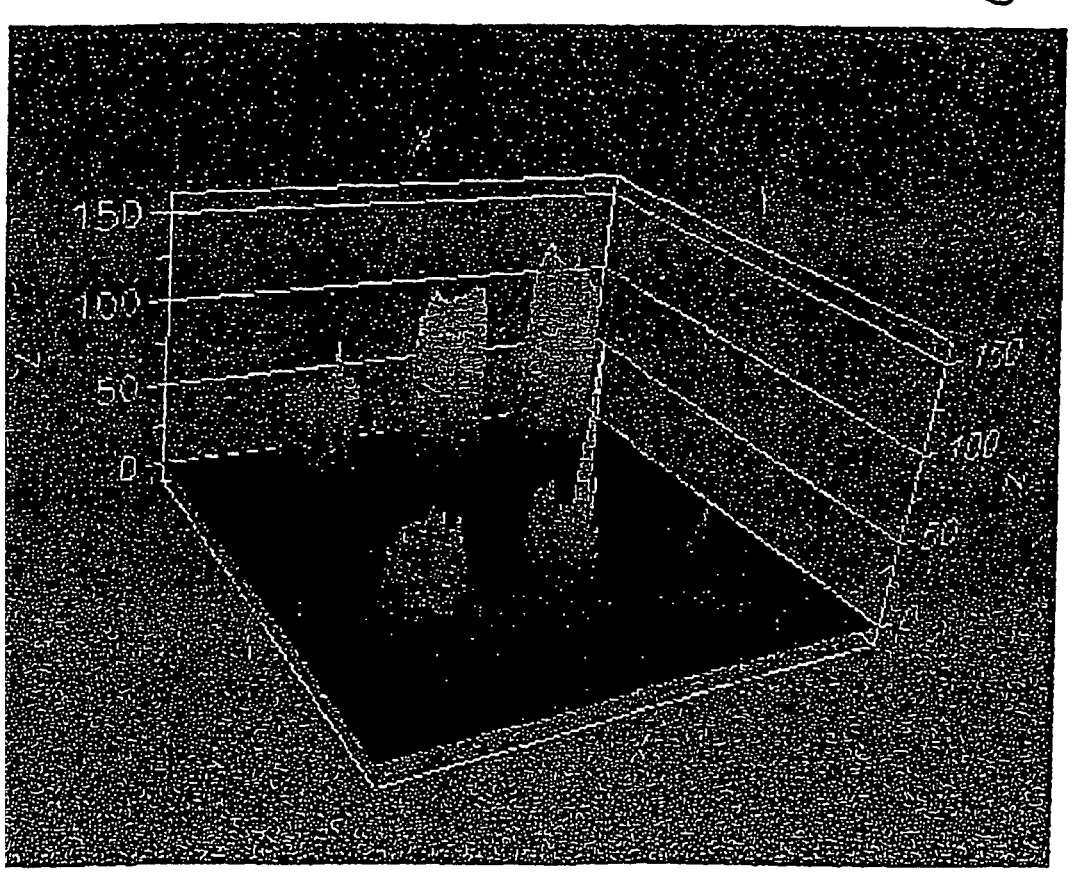

FIGS. 5A and 5B show the fluorescence of a detection system of the invention (glucose dehydrogenase and NAD$^+$) with increasing glucose concentration under a CCD camera.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood, reference is made to the following examples, which are intended to illustrate the invention, but not limit the scope thereof.

DETAILED DESCRIPTION

The following description of the preferred embodiment is merely exemplary in nature and is in no way intended to limit the invention or its application or uses.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may very from a stated reference without resulting in a change in the basic function of the subject matter at issue.

Example 1

Stoichiometric Detection of Glucose in the Glucose Dehydrogenase (GlucDH)/NAD$^+$ System in a Cuvette 100 mg/ml GlucDH are dissolved in buffer of pH 7 and mixed with the appropriate amount of NAD$^+$. On addition of increasing amounts of glucose, an increase in the fluorescence can be detected visually under a UV lamp (excitation wavelength 366 nm) (FIGS. 5A and 5B).

The solution with the enzyme system does not fluoresce without glucose. Nor do glucose and NAD$^+$ result in any fluorescence.

Example 2

Detection of Glucose in the GlucDH/NAD$^+$ System in a Polymer Film

A suspension of the following substance was mixed in a plastic test tube

Formula 1

| Substance | Amount [g] | Weight [%] |
|---|---|---|
| Acrylamide | 2.5 | 22.02 |
| Methylenebisacrylamide | 0.7 | 6.17 |
| 2,2-Dimethoxy-2-phenylacetophenone | 0.05 | 0.44 |
| Glycerol | 5 | 44.05 |
| Hydroxyethyl methacrylate | 1.4 | 12.33 |
| Methyl methacrylate | 0.4 | 3.52 |
| Crodasinic O solution, pH 8, 0.3 g/1000 ml | 1 | 8.81 |
| N,N'-(1,2-Dihydroxyethylene)bisacrylamide | 0.3 | 2.64 |
| TOTAL | 11.35 | 100 |

0.5 ml of this suspension were mixed with 0.5 ml of a solution of GlucDH (100 mg/ml), and the mixture was homogenized free of air bubbles in an ultrasonic bath.

The clear solution was poured onto a corona-treated polycarbonate sheet 125 mm thick and illuminated with a conventional illumination apparatus (Isel UV illumination device 2) for 20 min. The sheet was briefly washed with water and then dried in the air.

The resulting layer thickness was <2 μm. A freshly prepared glucose/NAD$^+$ solution (GKL-3 solution, 300 mg/dl glucose, 1 ml/6.4 mg of NAD$^+$) was spotted on the film. A strong fluorescence was immediately visible under a UV lamp.

Example 3

Adding a UV Absorber to Influence the Layer Thickness

A polymer layer comprising a blue dye (absorption maximum≈650 nm) for better identification was produced (formula 2). In a further experiment, a yellow dye was admixed as UV absorber to the initial formula (formula 3).

Formula 2

| Substance | Amount | Weight [%] |
| --- | --- | --- |
| Acrylamide | 37.5 g (0.53 mol) | 25.78 |
| Polyethylene glycol diacrylate, Mw ≈ 575 g/mol | 52.5 g (ca. 0.96 mol) | 36.10 |
| Solution of Crodasinic O (0.3 g/1 l) | 50 g | 34.38 |
| 4-Vinylbenzenesulfonic acid | 5 g | 3.44 |
| 2,2-Dimethoxy-2-phenylacetophenone photoinitiator | 350 mg | 0.24 |
| New methylene blue N | 100 mg | 0.06 |
| TOTAL | 145.45 g | 100 |

The mixture was homogenized by stirring and by ultrasonic bath treatment, distributed with a pipette on a 140 μm Pokalon sheet (corona-treated, stage 4) and illuminated in a UV illumination device (Actina U4, W. Lemmen GmbH) for 1 min. The resulting layer thickness was measured with a screw gage and was 240.5 μm.

Formula 3

| Substance | Amount | Weight [%] |
| --- | --- | --- |
| Formula 2 | 1 ml | ca. 99.99 |
| Mordant Yellow 7 (No. 686) (UV absorber) | 0.0001 g | 0.001 |
| TOTAL | ca. 1.0001 g | 100 |

The mixture was distributed on a sheet and then polymerized as described above. The resulting layer thickness was measured with a screw gage and was 79.3 μm.

This experiment shows that it is possible to influence the layer thickness. With reaction conditions which were otherwise the same, the layer thickness without UV absorber is 240.5 μm (see above); only 79.3 μm with UV absorber (Mordant Yellow 7).

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limed to these preferred aspects of the invention.

What is claimed is:

1. An apparatus for detecting an analyte in a sample, the analyte being present in the sample only up to a predetermined maximum possible concentration, the apparatus comprising:
    (a) a support configured to receive a first volume of the sample; and
    (b) a detection reagent provided on the support, the detection reagent comprising an enzyme-coenzyme complex, the detection reagent being provided in an amount such that the amount of enzyme-coenzyme complex is at least stoichiometric relative to the amount of analyte present in the sample;
    wherein the enzyme-coenzyme complex is selected and configured to participate in a reaction with the analyte, and wherein the detection reagent does not include any mediator capable of reacting with the coenzyme.

2. The apparatus as claimed in claim 1, wherein the enzyme of the enzyme-coenzyme complex comprises an oxidoreductase and wherein the complex is further selected and configured such that the reaction of the complex with the analyte produces one or more reaction products including detectable amounts of an oxidized form or a reduced form of the coenzyme.

3. The apparatus as claimed in claim 2, wherein the complex is further selected and configured such that the amounts of the oxidized form or the reduced form of the coenzyme produced in the reaction products are detectable in about 5 seconds or less from the start of the reaction.

4. The apparatus as claimed in claim 2, wherein the amounts of the oxidized form or reduced form of the coenzyme are detectable by optical methods.

5. The apparatus as claimed in claim 1, wherein the coenzyme of the enzyme-coenzyme complex is selected from nicotine derivatives.

6. The apparatus as claimed in claim 1, wherein the enzyme-coenzyme complex is embedded in a gel matrix.

7. The apparatus as claimed in claim 6, wherein the gel matrix has a layer thickness of $\leq 50$ μm.

8. The apparatus as claimed in claim 1, wherein the support is at least partly optically transparent.

9. The apparatus as claimed in claim 1, wherein the support comprises an essentially planar structure.

10. The apparatus as claimed in claim 1, wherein the support comprises a plurality of different detection reagents.

11. The apparatus as claimed in claim 1, wherein the sample comprises a body fluid.

12. The apparatus as claimed in claim 11, wherein the body fluid comprises blood and the analyte comprises glucose.

* * * * *